United States Patent
Caslaru et al.

(10) Patent No.: US 9,702,789 B2
(45) Date of Patent: Jul. 11, 2017

(54) METHOD AND APPARATUS FOR DISTRIBUTING PARTICULATE MATERIAL ALONG A TIRE FOOTPRINT DURING TIRE TEST

(71) Applicants: Robert Caslaru, Charlotte, NC (US); Samuel E. Hart, Jr., Travelers Rest, SC (US); Cedric W. Mousseau, Simpsonville, SC (US); Trevor W. Davis, Greer, SC (US); Robert Martin Falk, Mauldin, SC (US)

(72) Inventors: Robert Caslaru, Charlotte, NC (US); Samuel E. Hart, Jr., Travelers Rest, SC (US); Cedric W. Mousseau, Simpsonville, SC (US); Trevor W. Davis, Greer, SC (US); Robert Martin Falk, Mauldin, SC (US)

(73) Assignees: Compagnie Generale des Etablissements Michelin, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 99 days.

(21) Appl. No.: 14/439,143

(22) PCT Filed: Oct. 31, 2012

(86) PCT No.: PCT/US2012/062876
§ 371 (c)(1),
(2) Date: Apr. 28, 2015

(87) PCT Pub. No.: WO2014/070177
PCT Pub. Date: May 8, 2014

(65) Prior Publication Data
US 2015/0292984 A1   Oct. 15, 2015

(51) Int. Cl.
*G01M 17/02* (2006.01)
*G01N 3/02* (2006.01)

(52) U.S. Cl.
CPC ........ *G01M 17/024* (2013.01); *G01M 17/022* (2013.01); *G01N 3/02* (2013.01); *G01M 17/02* (2013.01)

(58) Field of Classification Search
USPC .......................................................... 73/146
See application file for complete search history.

(56) References Cited

U.S. PATENT DOCUMENTS 1,669,622 A   5/1928   Messer
2,010,049 A * 8/1935   Abbott, Jr. .......... G01M 17/022
                                                        73/8

(Continued)

FOREIGN PATENT DOCUMENTS

CA   2593751 A1   8/2006
DE   10141973 C1  4/2003

(Continued)

OTHER PUBLICATIONS

PCT/US2012/062876 nternational Search Report & Written Opinion, Jan. 23, 2013, 23 pages.

(Continued)

*Primary Examiner* — Paul West
*Assistant Examiner* — Mark A Shabman
(74) *Attorney, Agent, or Firm* — Hahn Loeser & Parks LLP

(57) ABSTRACT

The present invention comprises apparatus and methods for testing a tire on a wheel. Particular embodiments of such methods include providing a tire testing surface upon which the tire is to operate and a tire having a radially outer annular side including a road-engaging surface. The methods further include engaging forcefully a radially outer annular side of (Continued)

the tire with the tire testing surface to create a footprint constituting an area of contact between the tire and the tire testing surface, the footprint having a width extending in an axial direction of the tire. The tire is then rotated while engaged with the tire testing surface according to the prior step and a particulate is discharged from a particulate discharge outlet of a particular discharging device, the outlet having a length extending at least substantially across the width of the footprint.

21 Claims, 5 Drawing Sheets

(56) References Cited

U.S. PATENT DOCUMENTS

| | | |
|---|---|---|
| 2,098,306 A | 11/1937 | Porter |
| 2,598,599 A | 5/1952 | Pleasance |
| 2,766,618 A | 10/1956 | Stiehler et al. |
| 3,140,887 A * | 7/1964 | Wallace ............... B61C 15/10 |
| | | 291/1 |
| 4,174,204 A | 11/1979 | Chase |
| 4,476,515 A | 10/1984 | Coffee |
| 4,647,471 A | 3/1987 | Jenkins |
| 4,718,759 A | 1/1988 | Butler |
| 4,800,688 A | 1/1989 | Suzuki |
| 4,940,503 A | 7/1990 | Lindgren et al. |
| 5,111,687 A | 5/1992 | Hill |
| 5,365,702 A | 11/1994 | Shank, Jr. |
| 5,504,968 A | 4/1996 | Pressley |
| 5,636,681 A | 6/1997 | Sulzer et al. |
| 5,687,906 A | 11/1997 | Nakagawa |
| 5,703,284 A | 12/1997 | Gerhards et al. |
| 5,868,326 A | 2/1999 | Speegle |
| 6,021,962 A | 2/2000 | Hedger |
| 6,050,876 A | 4/2000 | Ouyang et al. |
| 6,439,041 B1 * | 8/2002 | Stalnaker ............ G01M 17/022 |
| | | 73/146 |
| 6,502,454 B1 | 1/2003 | MacIoce, Jr. et al. |
| 6,510,733 B2 | 1/2003 | Coe et al. |
| 6,546,791 B2 | 4/2003 | Yurjevich |
| 6,554,210 B2 | 4/2003 | Holt et al. |
| 7,036,753 B2 | 5/2006 | Huffman |
| 7,168,307 B2 | 1/2007 | Jahn et al. |
| 7,169,307 B2 | 1/2007 | Liu |
| 7,240,708 B2 | 7/2007 | Nomura et al. |
| 7,254,996 B2 | 8/2007 | Ouyang |
| 7,396,593 B2 | 7/2008 | Liu et al. |
| 8,123,147 B2 | 2/2012 | Fulkerson et al. |
| 8,196,462 B2 | 6/2012 | Stalnaker et al. |
| 2002/0071957 A1 | 6/2002 | Squitieri |
| 2003/0094120 A1 | 5/2003 | Golley et al. |
| 2004/0163455 A1 | 8/2004 | Deniau |
| 2005/0208225 A1 | 9/2005 | Sakata |
| 2007/0086861 A1 | 4/2007 | Pratt |
| 2007/0240614 A1 | 10/2007 | Lynch |
| 2008/0060574 A1 | 3/2008 | Bacchus et al. |
| 2009/0012763 A1 | 1/2009 | Langer et al. |
| 2010/0258014 A1 | 10/2010 | Van Heijningen |
| 2011/0000292 A1 | 1/2011 | Yoshikawa et al. |
| 2012/0186324 A1 | 7/2012 | Neugebauer et al. |

FOREIGN PATENT DOCUMENTS

| | | |
|---|---|---|
| GB | 161621 A | 4/1921 |
| GB | 326651 A | 3/1930 |
| GB | 2264503 A | 9/1993 |
| JP | 3044532 A | 2/1991 |
| JP | 04169673 A | 6/1992 |
| JP | 04181142 A | 6/1992 |
| JP | 04070288 B2 | 11/1992 |
| JP | H04343794 A | 11/1992 |
| JP | 6129954 A | 5/1994 |
| JP | 3706637 B2 | 9/1994 |
| JP | 7020030 A | 1/1995 |
| JP | H07020029 A | 1/1995 |
| JP | H07146217 A | 6/1995 |
| JP | H0850082 A | 2/1996 |
| JP | H08178815 A | 7/1996 |
| JP | H08233716 A | 9/1996 |
| JP | 11218470 A | 8/1999 |
| JP | 2001242056 A | 9/2001 |
| JP | 3739029 B2 | 1/2006 |
| JP | 2006226695 A | 8/2006 |
| JP | 2007017423 A | 1/2007 |
| JP | 2008014667 A | 1/2008 |
| JP | 2008082709 A | 4/2008 |
| JP | 2008134080 A | 6/2008 |
| JP | 2009122027 A | 6/2009 |
| JP | 04371940 B2 | 11/2009 |
| JP | 4496054 B2 | 7/2010 |
| JP | 4559617 B2 | 10/2010 |
| JP | 4609806 B2 | 10/2010 |
| JP | 4915139 B2 | 4/2012 |
| KR | 10-0642992 B1 | 11/2006 |
| KR | 10-0783660 B1 | 12/2007 |
| KR | 100783660 B1 | 12/2007 |
| WO | 02/12880 A2 | 2/2002 |
| WO | 03/014694 A2 | 2/2003 |
| WO | 2004046001 A2 | 6/2004 |
| WO | 2005116638 A1 | 12/2005 |
| WO | 2012003314 A1 | 1/2012 |

OTHER PUBLICATIONS

Neithalath et al; Using the Tire-Pavement Test Apparatus to Investigate the Influence of Time Geometry; paper 6, vol. 1, No. 1, 18 pgs, obtained from "http://www.concretepavements.org/IJCP/Vol%201%20No%201/Neithalath%20paper%206%20volume%201%20number%201.pdf".

Emil Venere; Machine harnesses sound science to probe causes of road noise, Mar. 25, 2003, 5 pgs, obtained from http://www.purdue.edu/uns/html3month/030325.Bernhard.tiremach.html.

Walraven, Perry; "Laboratory Tread Wear Simulation"; MTS Systems Corporation; 28 pages; presented at a meeting of the Rubber Division, American Chemical Society, Cleveland, Ohio, Oct. 17-20, 1995.

\* cited by examiner

METHOD AND APPARATUS FOR DISTRIBUTING PARTICULATE MATERIAL ALONG A TIRE FOOTPRINT DURING TIRE TEST

This application is a National Stage application of International Application No. PCT/US2012/062876, filed Oct. 31, 2012.

BACKGROUND OF THE INVENTION

This invention relates generally to the application of particulate material along a tire footprint during tire testing operations.

DESCRIPTION OF THE RELATED ART

Tires are often tested to determine any of a variety of characteristics. In particular instances, in lieu of testing tires on a vehicle, where conditions are difficult to control, tires are tested on a manufactured tire testing surface, such as the annular outer surface of a rotating road wheel, to better control the test conditions. Still, improvements to tire testing along manufactured tire testing surfaces remain necessary to better achieve more consistent or accurate results.

Manufactured tire testing surfaces may be employed by any of a variety of testing machines or systems. As such, tire testing surfaces may form generally flat or annular surfaces. For example, an annular tire operating surface may extend around a road wheel.

In operation, the tire is forcefully applied against, and rotates along the manufactured tire testing surface, such as the radially outer annular surface of the road wheel. In certain tests, particulate material comprising talc is applied to the tire and/or the manufactured tire testing surface for use along a tire footprint, the tire footprint comprising the area of contact between the tire and the wheel. In trying to better attain more consistent or accurate tire testing results, it has been found that the distribution of particulate material affects the tire testing results. Because the distribution of particulate material can impact tire testing results, and, in particular, the wear rate of the tire tread during such testing, there is a need to provide an improved distribution of particulate material along the road wheel.

SUMMARY OF THE INVENTION

The present invention comprises methods and apparatus for distributing particulate material along a tire testing surface. Particular methods of the present invention include a method for testing a tire on a wheel. Such methods include providing a tire testing surface and providing a tire having a radially outer annular side including a road-engaging surface. Such embodiments also include engaging forcefully a radially outer annular side of the tire with the tire testing surface to create a footprint constituting an area of contact between the tire and the tire testing surface, the footprint having a width extending in an axial direction of the tire. Furthermore, such methods include rotating the tire while engaged with the tire testing surface according to the prior step and discharging a particulate material from a particulate discharge outlet, the outlet having a length extending at least substantially across the width of the footprint.

Further embodiments of the invention comprise a tire testing device. Specific embodiments of the device comprise a tire testing surface and a tire retention member configured to rotatably retain a tire and arrange the tire in a tire testing surface-engaging position. Such devices further comprise a particulate discharging device having a particulate discharge outlet for discharging a flow of particulate material, the outlet having a length extending at least substantially across a width of a tire footprint, the footprint comprising an area of contact formed between a radially outer annular side of the tire and the tire testing surface when the tire is in the tire testing surface-engaging position.

The foregoing and other objects, features and advantages of the invention will be apparent from the following more detailed descriptions of particular embodiments of the invention, as illustrated in the accompanying drawings wherein like reference numbers represent like parts of the invention.

DETAILED DESCRIPTION OF PARTICULAR EMBODIMENTS

Figure 1:
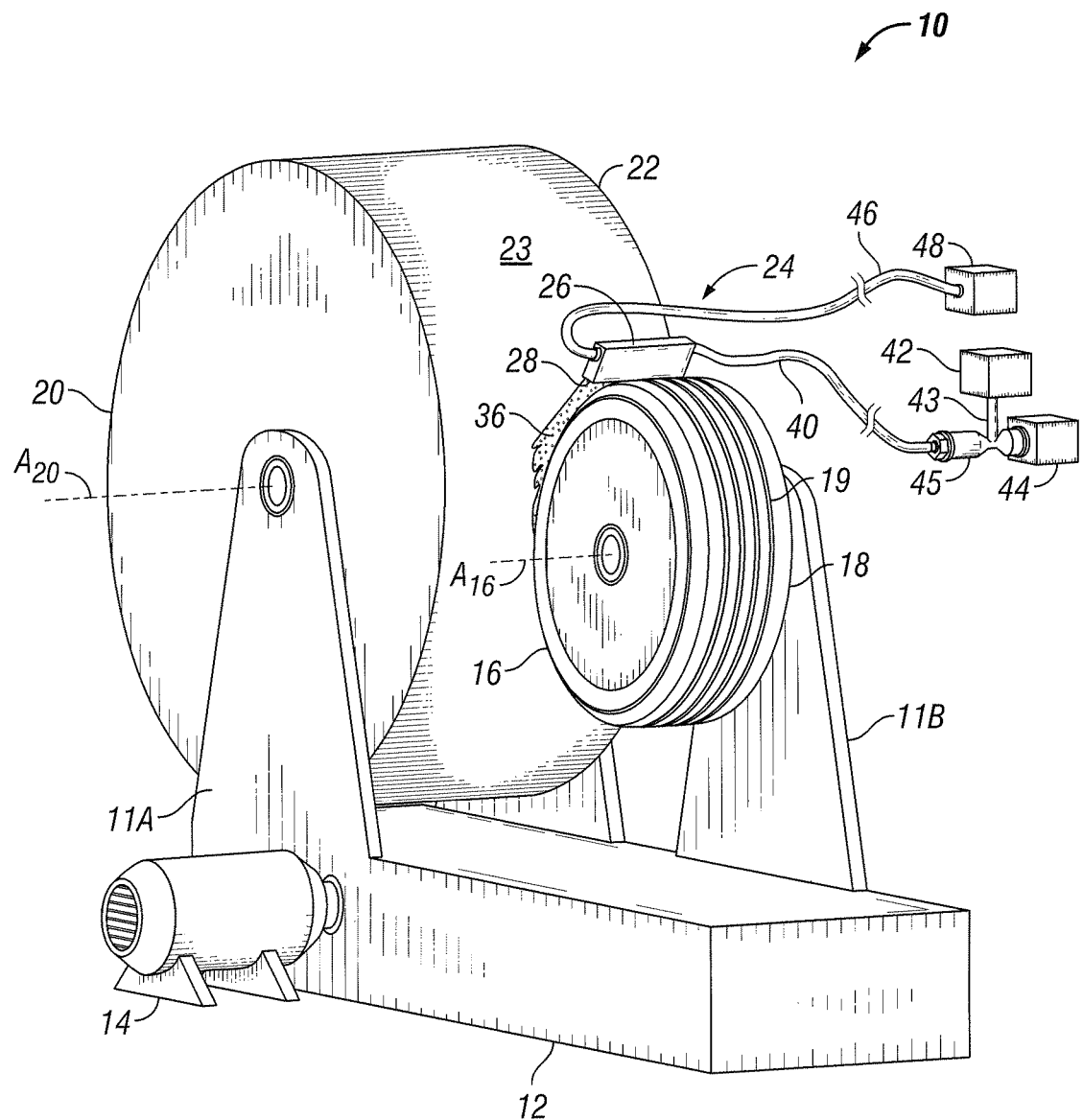
FIG. 1 is a perspective view of a tire testing device comprising a machine including a road wheel upon which a tire operates to evaluate the performance of the tire, a particulate discharging device arranged to direct a flow of particulate material along a footprint of the tire formed along an outer annular tire testing surface of the road wheel in accordance with a particular embodiment of the invention.

As suggested above, there is a need to provide improved distribution of particulate material, such as talc, along a tire footprint formed between a the tire and a manufactured tire testing surface during tire testing operations.

It has been found that the distribution of particulate material along a tire footprint during tire testing along a manufactured tire testing surface can negatively impact tire testing results. In particular, it has been found that the prior art methods and devices for distributing particulate material along a tire footprint formed on a road wheel results in a substantially uneven distribution of particulate. "Manufactured tire testing surface" and "tire testing surface," as used synonymously herein unless otherwise noted, reference a tire operating surface that has been formed along or in association with a tire testing device, such as a tire testing machine, having a surface upon which a tire operates which is formed of any desired material, whether synthetic or natural, and which may form any desired surface upon which the tire is to be evaluated, such as a surface that forms or simulates a real-world tire operating surface. In an effort to provide more consistent and accurate test results, methods and apparatus for improving the distribution of particulate material along a tire footprint are discussed below.

In particular embodiments, a method of testing tires includes a step of providing a tire testing surface. It is understood that the tire testing surface may comprise any testing surface known to one of ordinary skill in the art, whether flat or contoured. For example, the tire testing surface may be arranged along a radially outer annular side of a road wheel, where the tire testing surface forms an annular surface. The radially outer annular side is located radially outward a rotational axis of the wheel along an outer extent of said wheel. The road wheel may comprise any wheel for use in tire testing, where the wheel is configured to rotate and the tire operating surface is configured to engage a tire during operation. It is understood that the tire testing surface may include any desired texture and may extend continuously or intermittently around the outer annular side of the wheel. For example, the wheel may have texture that promotes tire wear or that generates sufficient friction to create a slip angle within the tire footprint as the tire rotates side-to-side relative the tire operating surface to simulate the turning of a vehicle.

Particular embodiments of such methods further include a step of providing a tire having a radially outer annular side including a road-engaging surface, the tire being rotatably retained on a tire retention member. The tire provided may comprise any tire. For example, the tire may comprise a pneumatic tire or a non-pneumatic tire, whereby a solid band including a tread layer is arranged along a wheel or the like, such as is commonly used with skid steers. In many embodiments, the radially outer annular side of the tire includes a tread, the tread forming the road-engaging surface upon which the tire rotates and engages the wheel. The tire includes a rotational axis extending in an axial direction of the tire. It is understood that the tire may be rotatably retained on a retention member to facilitate rotation of the tire along the tire testing surface. It is understood that the retention member may comprise any member or device configured to rotatable retain a tire that is known to one of ordinary skill in the art. For example, the retention member may be an axle or spindle.

Particular embodiments of such methods further include a step of engaging forcefully the radially outer annular side of the tire with the tire testing surface to create a footprint constituting an area of contact between the tire and the tire testing surface, the footprint having a width extending in an axial direction of the tire. The step of engaging may comprise translating either or both of the tire and the tire testing surface towards the other to generate engagement between the tire and the wheel. The translation may be performed by any known method or device. Upon engagement, an area of contact between the tire and the tire testing surface is generated, which is referred to as a tire footprint. It is understood that the tire may engage the tire testing surface in any desired arrangement. For example, when the tire testing surface is arranged along a road wheel, the axes of rotation of each the tire and wheel may be parallel or biased from a parallel arrangement.

Particular embodiments of such methods further include a step of rotating the tire while engaged with the tire testing surface according to the prior step. Once the tire and tire testing surface are engaged, the tire rotates along the surface. In particular embodiments, the tire testing operation also rotates, such as when the tire testing surface is arranged along a road wheel. In any event, rotation is facilitated by any known method or device. For example, the tire and/or wheel may be driven to accomplish the step of rotating. In doing so, a drive source is arranged in operable communication with tire and/or the wheel. The drive source may comprise any drive source known to one of ordinary skill in the art, and may comprise, for example, a motor. It is also understood that rotating the tire may be achieved by rotation of the tire testing surface, and vice versa.

Particular embodiments of such methods further include a step of discharging a particulate material from an forming a particulate discharge outlet of a particulate discharging device across a full width of the footprint. In an effort to improve the distribution of particulate material across the footprint of a tire operating along a tire testing surface, a particulate material is discharged from an forming a particulate discharge outlet of a particulate discharging device, the outlet comprising one or more apertures. In such embodiments, the outlet forms a particulate discharge outlet of a particulate-receiving chamber arranged within the particulate discharging device. The particulate-receiving chamber receives the particulate from a particulate inlet prior to the step of discharging a particulate. It is understood that the particulate may comprise any desired particulate material, including talc. The particulate may be supplied in any desired form. For example, in particular embodiments, the particulate comprises a gas-particulate mixture. The gas-particulate mixture may be formed by employing any known method or device, such as by using a venturi mixer. It is further understood that the mixture may be formed from any desired particulate, such as talc, and any desired gas, including a gas mixture such as atmospheric air. Furthermore, it is understood that the particulate discharging device may comprise a single aperture, and the particulate discharging device may comprise an air knife or any other similar device.

In the embodiments previously discussed, the particulate discharge outlet discharges a particulate material across a full width of the footprint. In doing so, the particulate discharge outlet may have a length that is at least equal to the full width of the footprint, although it is understood that the particulate discharge outlet may have a length extending less the entire full width of the footprint even thought the outlet still discharges the particulate material across the full width of the footprint. Accordingly, the particulate discharge outlet may be configured to discharge particulate material across a full width of the footprint whether or not the outlet has a length extending greater than or equal to the full width of the footprint or less than the full width of the footprint. For example, the discharge path of the particulate material may be angular, meaning the path may extend further outward along a lengthwise direction of the particulate discharge outlet such that the discharge of particulate material extends in a lengthwise direction beyond the full length of the outlet. By further example, the particulate discharge outlet has a length extending at least substantially across the width of the footprint, where "substantially across the width of the footprint" means that while the particulate discharge outlet length may not extend fully across the entire width of the footprint, the particulate discharge outlet extends sufficiently across a majority of the footprint width to discharge the particulate material across the full width of the footprint. In other variations, the length of the particulate discharge outlet extends at least substantially across a full width of the tread, the width of the tread extending in the axial direction of the tire or, in other words, laterally between opposing sidewalls of the tire. It is understood that the particulate may be discharged from the particulate discharge outlet at any rate.

In particular examples, particulate material is discharged from the particulate discharge outlet at a rate of 1 gram to 9 grams per minute or at a rate of at least 6 grams per minute.

It is appreciated that the particulate discharge outlet, as well as any one or more apertures forming the outlet, may comprise any desired shape. For example, the width of the particulate discharge outlet may remain constant along the length of the particulate discharge outlet, such as where the particulate discharge outlet is rectangular. In other variations, a width of the particulate discharge outlet varies along the length of the particulate discharge outlet, and may vary linearly or non-linearly, which includes a curvilinear variation. By example, the particulate discharge outlet may form an oval. By further example, the width of the particulate discharge outlet may taper along the length of the particulate discharge outlet, such as from a maximum width to a minimum width or vice versa. It is noted that the particulate discharge outlet width extends perpendicular to the particulate discharge outlet length, and in certain instances, the particulate discharge outlet width is less than the particulate discharge outlet length although it is appreciated that the width and length may be equal, such as when the particulate discharge outlet is circular or forms a regular quadrilateral (i.e., a square).

Particular embodiments of such methods include a step of injecting a burst of gas into a particulate-receiving chamber of the device to dislodge any particulate remaining within the discharging chamber after initiating the step of discharging a particulate material from a particulate discharge outlet. Once the step of discharging a particulate material from an particulate discharge outlet has initiated, a burst of gas may be injected into the particulate-receiving chamber of the device to remove any particulate remaining within at least a portion of the chamber. The burst of gas has sufficient velocity and volume to provide sufficient force to dislodge, eject, or expel any particulate that may have built-up or otherwise become retained or lodged within the chamber. For example, the burst of gas may endure for up to one second before terminating. Because the step of discharging a particulate material may continue or repeat, the step of injecting a burst of gas may be repeated periodically. While the step of injection is performed after a step of discharging a particulate has initiated, which provides the particulate retained within the chamber in need of removal, the step of injecting may be performed while the step of discharging endures (that is, were the step of injecting is performed concurrently with a step of discharging), or may occur after a step of discharging has terminated or been paused temporarily. It is understood that the supply of gas may comprise the same gas source that may be employed to supply a gas-particulate mixture, or any other gas source.

These methods for distributing particulate material into a tire footprint arranged along a tire testing surface may be achieved manually or automatically, in whole or in part. Exemplary embodiments of a tire testing device for use in performing such methods are discussed in further detail below. The device(s) shown in the figures only exemplify any of a variety of tire testing devices that may be employed within the scope of this invention.

With reference to FIG. 1, an exemplary tire testing device 10 comprising a tire testing machine is shown. The machine 10 includes a base or housing 12 to which a tire 16 and a wheel 20 are rotatably attached (that is, configured to rotate). In particular, the wheel 20 is rotatably retained and operably attached to a wheel retention portion 11a. Wheel retention portion may comprise any member or device known to one of ordinary skill upon which any wheel may be securely mounted for purposes of performing the methods disclosed herein. Furthermore, the tire 16 is rotatably retained and operably attached a tire retention member 11b, which may comprise any member or device configured to rotatable retain a tire that is known to one of ordinary skill in the art. Additionally, the tire may mounted on a mounting member comprising a wheel, rim, or any other dimensionally fixed or expandable member upon which any tire may be securely mounted for purposes of performing the methods disclosed herein which may be known to one of ordinary skill. Any such mounting member may facilitate pressurization of the tire should the tire comprise a pneumatic tire, since tire 16 may comprise any pneumatic or non-pneumatic tire. A drive source 14 is also included for driving the wheel and/or the tire, which may comprise any drive source known to one of ordinary skill in the art, such as a motor.

With continued reference to FIG. 1, the wheel 20 includes a radially outer annular side 22 having a tire testing surface 23 to which the tread 19 of the tire 16 is forcefully applied and engaged with during tire testing operations. While the tire testing surface may extend discontinuously around the outer side, in the embodiment shown, the surface 23 extends lengthwise in a circumferential direction about the outer side 22 to form an annular surface, while the tread 19 forms a road-engaging surface along a radially outer annular side 18 of the tire 16. Rotational axes of the tire 16 and the wheel 20 are identified as $A_{16}$ and $A_{20}$, respectively.

Figure 2:
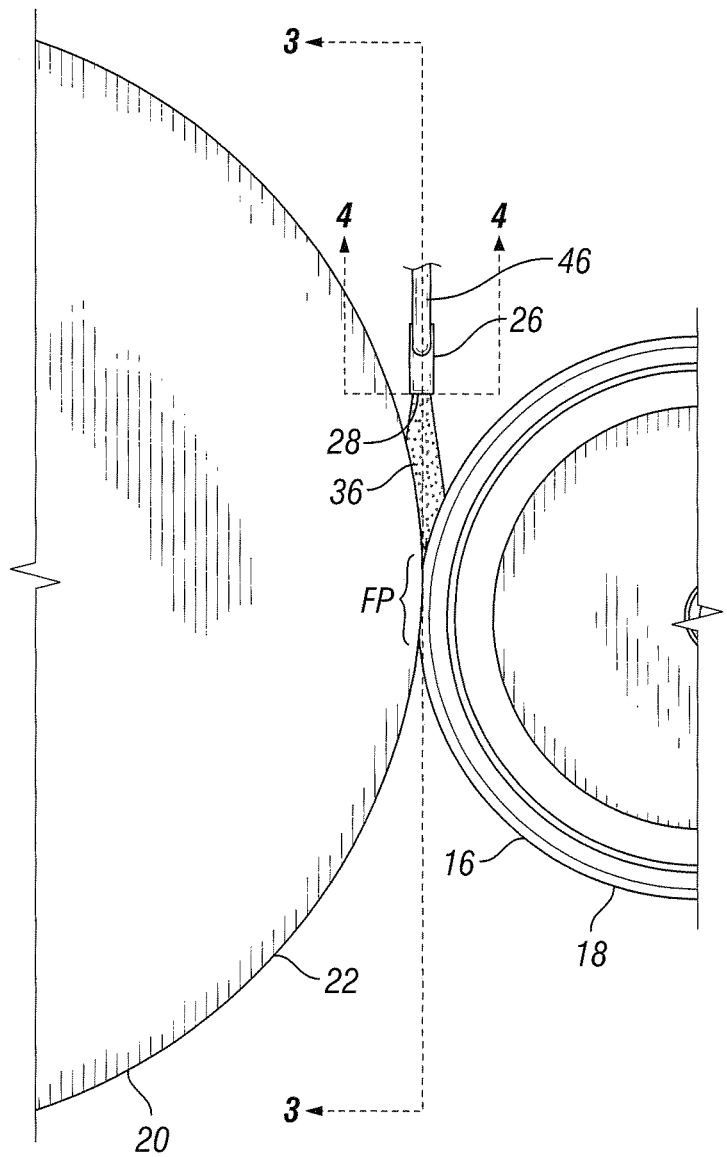
FIG. 2 is a side view of the tire testing device of FIG. 1.

The tire testing device 10 of FIG. 1 further includes a particulate discharging system 24 including a particulate discharging device 26 configured to discharge a flow of particulate material 36 for the purpose of applying particulate material along the tire footprint. The discharging device 26 shown generally describes an air knife, although device 26 may describe any other device similar in form or operation. In applying particulate material along the tire footprint, it is understood that the particulate material may be applied to portions of either or both of the tire testing surface 23 and the road-engaging surface 19 of the tire prior to each portion entering the tire footprint—that is, prior to a portion of the tire contacting a portion of the wheel as each rotates. In FIG. 2, a side view of the discharging device 26 is shown directing a flow of particulate material into a tire footprint FP.

As shown in FIGS. 1 and 2, the discharging device 26 is arranged in close relation, or adjacent, to the tire testing surface 23 and the road-engaging surface 19. "In close relation" means that the device is arranged in sufficient proximity to the radially outer annular sides of the wheel and/or of the tire such that the flow of particulate material being discharged from the discharging device is able to apply a desired amount of particulate material to the intended wheel and/or tire surfaces. It is appreciated that, in other variations, the discharging device 26 may be arranged in close relation, or adjacent, to either the tire testing surface 23 or the road-engaging surface 19, since the particulate material may be applied to either the wheel or the tire. In the embodiment shown in FIGS. 1 and 2, the flow of particulate material 36 is directed at the interface between the wheel and the tire, which is where the tire footprint FP is formed. In this arrangement, the flow may apply particulate material to the radially outer annular side of both the wheel and the tire.

The particulate discharging system 24 in FIG. 1 includes a delivery system for delivering particulate material to the discharging device 26 in accordance with an exemplary embodiment of the invention. In the delivery system shown, the particulate material is dispersed into a gas flow and supplied as a gas-particulate mixture forming a flow of particulate material. To facilitate delivery, the delivery system includes a supply conduit 40 operably attached to an inlet of discharging device 26, the supply conduit being arranged in operable communication with a supply of particulate material 42 and a gas flow source 44. It is understood that the gas and particulate material may be mixed according to any known device or method. In the device shown, a venturi mixer is employed, whereby the supply of particulate material 42 is fed into a venturi nozzle 45 by way of a feeding conduit 43, where the particulate material is fed into the conduit by a screw feeder or any other known feeding device or method. The gas employed may comprise air (a mixture of atmospheric gases), or any other desired gas or mixture of gases. Furthermore, the gas may be conditioned as desired before or after receiving the particulate material to form a gas-particulate mixture. For example, the gas or gas-particulate mixture may be conditioned to eliminate moisture or any other desired substance. By further example, the temperature of the gas, the particulate, or the gas-particulate mixture may be controlled. Accordingly, a heater or dryer may be employed to remove moisture and/or elevate the temperature of the particulate or gas. It is understood that the delivery system shown is exemplary, as any delivery system known to one of ordinary skill in the art may be employed to supply a flow of gas containing particulate material to the discharging device 26.

Device 26 generally comprises a housing formed of any desired material, such as aluminum or stainless steel. To reduce any unintentional retention of particulate within the device, the device or portions thereof, such as the particulate-receiving chamber, may be formed of, or coated with, a low-friction material or other material that reduces the ability of the particulate to adhere to the device. Additionally, or in the alternative, other features or methods may be employed to remove particulate that may accumulate within the device after gas-particulate mixture has been discharged from the device. For example, the device may be configured to inject a burst of gas into the discharging device to dislodge or remove any accumulated particulate. This may be achieved by utilizing the gas-particulate inlet 40 to provide the burst of gas, or one or more additional gas conduits may be operably attached to the discharging device 26. For example, with reference again to the embodiment of FIG. 1, a gas conduit 46 is operably attached to the discharging device 26. In particular embodiments, the gas flow discharged forms a brief burst of gas, which may be coordinated to occur periodically, such as at any desired time interval and for any desired amount of time. For example, the burst of gas may occur once every minute for up to one second (that is, one second or less). In any event, the burst may occur while the flow of particulate material is being discharged, or the flow of particulate material may be temporarily paused while the burst of gas flow occurs. It is understood that the gas flow may be discharged at any desired rate, for any duration, and at any desired pressure. Furthermore, and the gas may comprise any desired gas or gas mixture, such as atmospheric air. Additionally, the discharging device may employ a sensor to trigger a discharge of gas flow when sufficient accumulation arises by ascertaining whether any blockage of the particular discharge outlet exists. This may occur, for example, automatically by monitoring the flow of particulate material being discharged from the particulate discharge outlet. By further example, a sensor may monitor the device for any physical buildup of particulate material.

Figure 3:
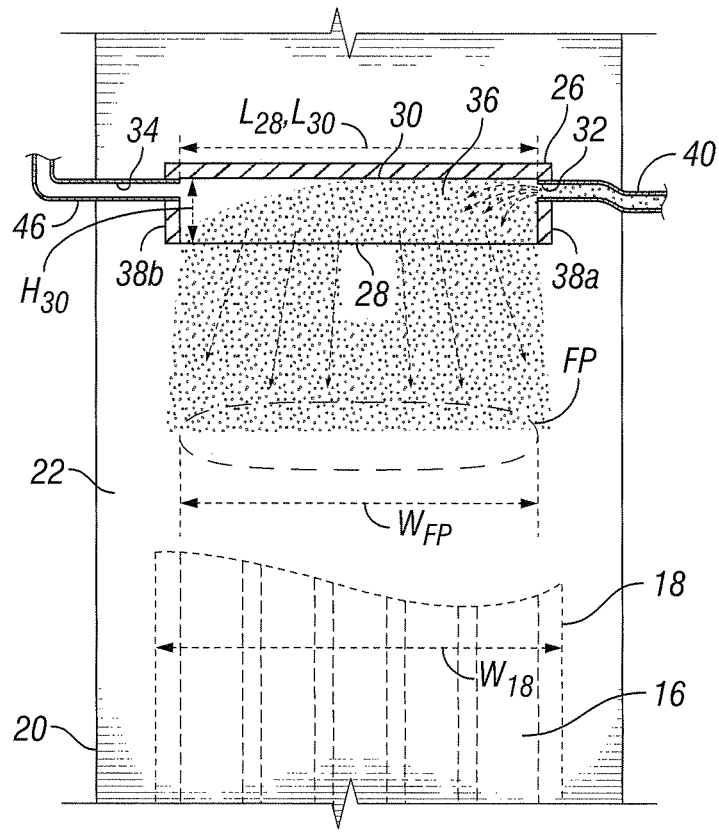
FIG. 3 is a sectional view of the tire testing device taken along line 3-3 in FIG. 2 showing the particulate discharging device applying particulate material into the tire footprint along the road wheel.

With particular reference to FIG. 3, the particulate discharge device 26 is shown in cross-section discharging particulate material 36 onto the radially outer annular side of the tire 16 and/or the wheel 20 for use within a tire footprint FP. In this view, the particulate discharge outlet 28 of the discharging device 26 is more clearly shown as forming the outlet of a particulate receiving chamber 30 of the device. In the embodiment shown, outlet 28 forms a single aperture but may comprise a plurality of apertures in other variations. As chamber 30 is configured to receive a flow of particulate material or a gas-particulate mixture from one or more inlets and discharge the same through one or more outlets 28, a particulate supply conduit 40 is arranged in communication with chamber 30 to supply chamber 30 with a gas-particulate mixture. To achieve this, device 26 includes a particulate inlet 32 for receiving supply conduit 40 on a first end 38a. To provide a burst of gas, if desired to dislodge any particulate accumulating within the chamber 30, the chamber includes a gas flow inlet 34 for receiving gas flow supply conduit 46 on a second, opposing end 38b of device 26. It is understood, that device 26 may include one or more particulate inlets 32 arranged at any location for receiving one or more particulate supply conduits. Likewise, it is also understood that device 26 may include one or more gas flow inlets 34 may be arranged at any location along device and relative any particulate inlet, regardless of whether a gas flow inlet is arranged opposite particulate inlet.

The particulate receiving chamber of the discharging device may comprise any shaped volume. For example, with reference to FIG. 3, the chamber 30 has a rectangular cross-sectional shape, but which may, in other variations, be altered by tapering or contouring the height $H_{30}$ and/or the length $L_{30}$ of the chamber to better control or direct the flow of particulate material from any particulate inlet 32 and through the outlet 28 of device 26. The tapering or contouring may also occur in a widthwise direction of the device, which is perpendicular to both the height $H_{30}$ and length $L_{30}$.

It is further noted that the embodiment of FIG. 3 more clearly shows the association between the length of the discharge outlet 28 and the tire 16 and footprint FP. As stated above, the length $L_{28}$ of the discharge device outlet 28 is shown to be at least equal to and greater than the width of Footprint FP. Furthermore, outlet length $L_{28}$ may also be equal to or greater than the tire tread width $W_{18}$.

Figure 4:
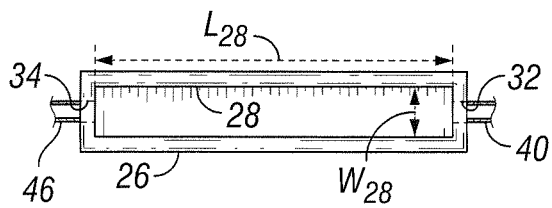
FIG. 4 is a sectional view of the tire testing device taken along line 4-4 in FIG. 2 showing a particulate discharge outlet of the discharging device.
Figure 5:
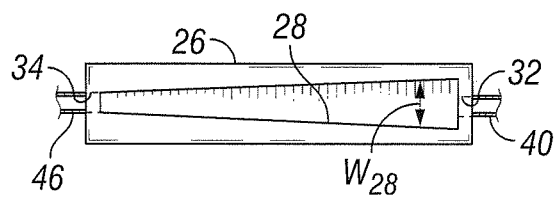
FIG. 5 is a sectional view of an alternative embodiment of the discharging device of FIG. 4 taken along line 4-4 in FIG. 2, wherein the width of the discharge opening tapers from a first end including an inlet for the particulate material to the opposing end of the discharging device.

It is understood that the discharge device outlet may comprise any desired shape. For example, with reference to FIG. 4, the outlet 28 has a constant length $L_{28}$ and a constant width $W_{28}$, which provide a rectangularly-shaped aperture. With reference now to FIG. 5, the outlet 28 is trapezoidly-shaped, whereby the width $W_{28}$ tapers or varies from a maximum value nearest particulate inlet 32 to a minimum value nearest the particulate outlet 34. It is understood, however, that the taper may be linear or non-linear, such as curvilinear.

Figure 6:
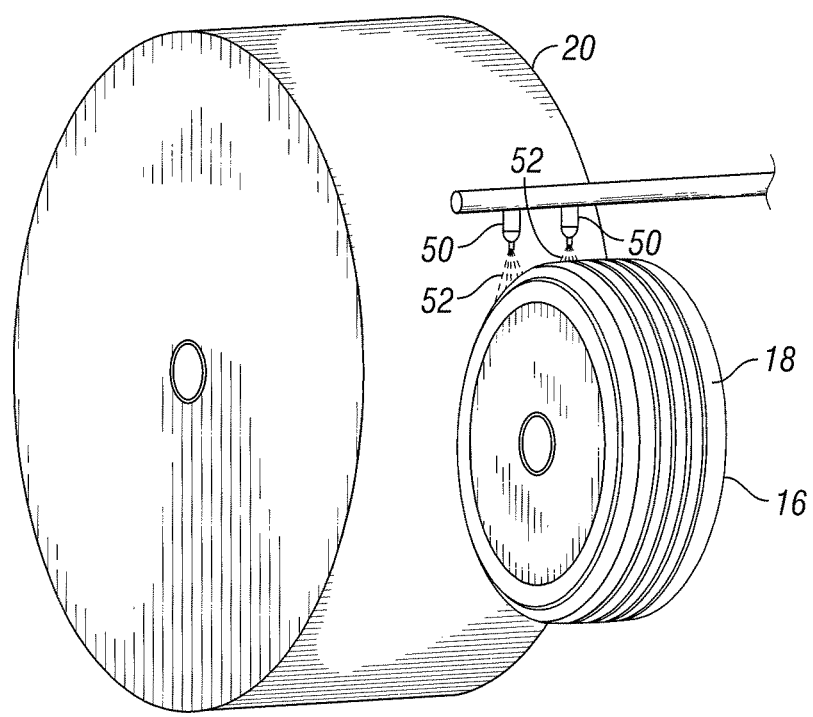
FIG. 6 is a perspective view of a prior art tire testing device which includes a pair of particulate discharging nozzles spaced across a width of the tire footprint.

In the prior art, with reference to FIG. 6, a pair of nozzles 50 has been employed to discharge particulate material comprising talc 52 for distribution along a tire footprint formed along a road wheel 20. The use of such nozzles, however, has provided a substantially uneven distribution of talc across a width of the tire footprint. The substantial uneven distribution of talc has been found to negatively impact the results of certain tire tests. By employing the inventive particulate discharging device and methods described above, a significant reduction in the unevenness has been achieved, which has been found to improve the results of the certain tire tests.

Figure 7:
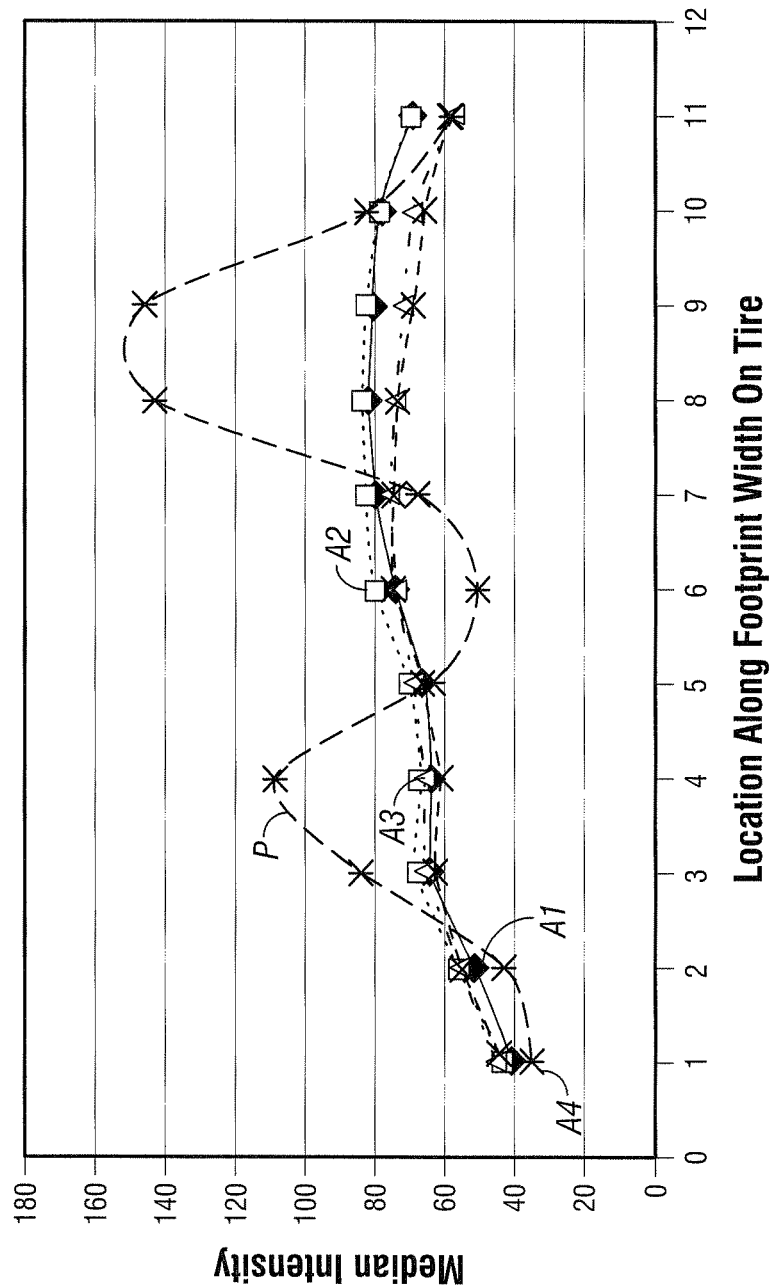
FIG. 7 is diagram showing the difference in particulate material distributions along a width of a tire footprint, between the airborne particulate discharge device of FIG. 1 and the pair of nozzles shown in FIG. 6.

With reference to FIG. 7, a chart is shown comparing a prior art distribution of talc 54 achieved using the prior art pair of nozzles (identified as series P in the figure) with a distribution of talc 56 using the inventive device and methods described above in four different tests to verify repeatability (which are identified as series A1, A2, A3, and A4 in the figure). In particular, an actual distribution of talc distributed along a footprint in accordance with the invention described above was obtained using tape situated along a tire tread, where the adhesive of the tape retained the particulate material distributed within a tire footprint arising during operation of the road wheel. The particulate coated tape was then analyzed to determine the distribution of the particulate material across the footprint width by measuring the intensity of the particulate at different locations along the width of the tire footprint. The chart in FIG. 7 shows the average intensity of the particulate material measured at different locations across the width of the footprint. According to the measurements obtained for the prior art distribution of talc, an approximately 300% variation was measured across the width of the footprint. In comparison, a 100% variation was measured across the width of the footprint. This equates to a 200% improvement using the inventive device and methods. As can be seen in the chart, a substantial dampening of the variation across the width of the footprint is achieved.

While this invention has been described with reference to particular embodiments thereof, it shall be understood that such description is by way of illustration and not by way of limitation. Accordingly, the scope and content of the invention are to be defined by the terms of the appended claims.

What is claimed is:

1. A method for testing a tire on a wheel, the method comprising:
    providing a tire testing surface;
    providing a tire having a radially outer annular side including a road-engaging surface, the tire being retained on a tire retention member;
    engaging forcefully the radially outer annular side of the tire with the tire testing surface to create a footprint constituting an area of contact between the tire and the tire testing surface, the footprint having a width extending in an axial direction of the tire;
    rotating the tire while engaging forcefully a radially outer annular side of the tire with the tire testing surface;
    discharging a flow of particulate material from a particulate discharge outlet of a particulate discharging device, the outlet having a length extending at least substantially across the width of the footprint; and
    injecting a burst of gas into a particulate-receiving chamber arranged within the particulate discharging device to dislodge any particulate material remaining within the particulate-receiving chamber after performing the step of discharging the flow of particulate material from the particulate discharge outlet.

2. The method of claim 1, where the tire testing surface comprises a radially outer annular side of a road wheel such that providing a tire testing surface also includes providing a road wheel configured to rotate.

3. The method of claim 1, wherein the particulate discharge outlet forms an outlet of the particulate-receiving chamber arranged within the particulate discharging device, the particulate-receiving chamber receiving the particulate material from an inlet prior to discharging the particulate material.

4. The method of claim 3, wherein the particulate discharging device has a single particulate discharge outlet.

5. The method of claim 3, wherein the inlet includes at least one supply conduit located on an end surface in a longitudinal direction of the discharge outlet in the particulate-receiving chamber.

6. The method of claim 5, wherein the at least one supply conduit is substantially transverse to the discharge outlet.

7. The method of claim 1, wherein injecting a burst of gas endures for up to one second before terminating.

8. The method of claim 7, wherein injecting a burst of gas is repeated periodically.

9. The method of claim 1, wherein the length of the particulate discharge outlet extends at least substantially across a full width of the tread, the width of the tread extending in the axial direction of the tire.

10. The method of claim 1, where the flow of particulate material is discharged from the particulate discharge outlet at a rate of 1 gram to 9 grams per minute.

11. The method of claim 1, where the particulate discharge outlet has a width that varies along the length of the particulate discharge outlet, the outlet width extending perpendicular to the outlet length and the outlet width being less than the outlet length.

12. The method of claim 11, where the width of the particulate discharge outlet tapers along the length of the outlet.

13. The method of claim 1, wherein the particulate discharging device is an air knife.

14. The method of claim 1, where a height of the particulate receiving chamber that is perpendicular to the width and the length of the particulate discharge outlet is contoured.

15. The method of claim 1, where the particulate-receiving chamber receives the particulate material from a particulate inlet and the particulate-receiving chamber receives the burst of gas from a gas flow inlet separate from the particulate inlet.

16. A tire testing device comprising:
    a tire testing surface;
    a tire retention member configured to rotatably retain a tire and arrange the tire in a tire testing surface-engaging position;
    a particulate discharging device having a particulate discharge outlet for discharging a flow of particulate material, the outlet having a length extending at least substantially across a width of a tire footprint, the footprint comprising an area of contact formed between a radially outer annular side of the tire and the tire testing surface when the tire is in the tire testing surface-engaging position; and
    a supply of gas in operable communication with the device and configured to provide a burst of gas into a particulate-receiving chamber arranged within the particulate discharge device to dislodge any particulate remaining within the particulate-receiving chamber after discharging a flow of particulate material from the particulate discharge outlet.

17. The device of claim 16, wherein the particulate discharging device has a single particulate discharge outlet.

18. The device of claim 16, where the particulate discharge outlet has a width that varies along the length of the particulate discharge outlet, the outlet width extending perpendicular to the outlet length and the outlet width being less than the outlet length.

19. The device of claim 16, wherein the particulate-receiving chamber arranged within the particulate receiving device receives the particulate material from an inlet, and the inlet is located on an end surface in a longitudinal direction of the discharge outlet in the particulate-receiving chamber.

20. The device of claim 16, wherein the particulate discharge device includes at least one supply conduit substantially transverse to the discharge outlet.

21. The device of claim 16, where the particulate-receiving chamber receives the burst of gas from a gas flow inlet separate from a particulate inlet.

* * * * *